(12) United States Patent
Cheng

(10) Patent No.: US 10,254,244 B1
(45) Date of Patent: Apr. 9, 2019

(54) BIOSENSOR HAVING A SENSING GATE DIELECTRIC AND A BACK GATE DIELECTRIC

(71) Applicant: INTERNATIONAL BUSINESS MACHINES CORPORATION, Armonk, NY (US)

(72) Inventor: Kangguo Cheng, Schenectady, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/729,733

(22) Filed: Oct. 11, 2017

(51) Int. Cl.
| G01N 27/403 | (2006.01) |
| G01N 27/414 | (2006.01) |
| G01N 33/487 | (2006.01) |
| C12Q 1/6825 | (2018.01) |
| H01L 29/66 | (2006.01) |
| H01L 29/78 | (2006.01) |
| H01L 29/423 | (2006.01) |

(52) U.S. Cl.
CPC ....... *G01N 27/4145* (2013.01); *C12Q 1/6825* (2013.01); *G01N 33/48707* (2013.01); *H01L 29/42364* (2013.01); *H01L 29/66484* (2013.01); *H01L 29/66666* (2013.01); *H01L 29/7827* (2013.01); *H01L 29/7832* (2013.01)

(58) Field of Classification Search
None
See application file for complete search history.

(56) References Cited

U.S. PATENT DOCUMENTS

| 5,466,348 | A | 11/1995 | Holm-Kennedy |
| 7,476,946 | B2 | 1/2009 | Bryant et al. |
| 8,963,216 | B2* | 2/2015 | Fife ..................... G01N 27/414 257/253 |
| 9,570,288 | B2 | 2/2017 | Rigante et al. |
| 2014/0054651 | A1 | 2/2014 | Bashir et al. |
| 2014/0295573 | A1 | 10/2014 | Huang et al. |
| 2017/0059513 | A1 | 3/2017 | Afzali-Ardakani et al. |
| 2017/0160226 | A1 | 6/2017 | Huang et al. |
| 2017/0205371 | A1 | 7/2017 | Liu et al. |
| 2017/0227533 | A1* | 8/2017 | Lin ..................... H01L 51/0512 |

* cited by examiner

*Primary Examiner* — Nishath Yasmeen
(74) *Attorney, Agent, or Firm* — F. Chau & Associates, LLC

(57) ABSTRACT

A vertical biosensor includes a substrate and a source disposed on the substrate. A bottom spacer is disposed on the source. A chamber is disposed on the bottom spacer. A sensing gate dielectric is disposed on side and bottom surfaces of the chamber. A fin channel is disposed on opposite sides of the chamber along a direction parallel to an upper surface of the substrate facing the chamber. A back gate dielectric is disposed on the fin channel. A drain is positioned above the fin channel along a direction orthogonal to an upper surface of the substrate. A thickness of the back gate dielectric is greater than a thickness of the sensing gate dielectric.

13 Claims, 10 Drawing Sheets

BIOSENSOR HAVING A SENSING GATE DIELECTRIC AND A BACK GATE DIELECTRIC

BACKGROUND

The present invention generally relates to a biosensor, and more particularly to a biosensor including a sensing gate dielectric and a back gate dielectric Biosensors may have a variety of applications. For example, a biosensor may be used in DNA sequencing or virus screening. Additionally, biosensors may be employed to detect a biocharge in DNA, protein, and cancer cells. As an example, detection of a biocharge may be correlated with an amount of DNA present in a chamber. Thus, a biosensor employing biocharge detection may be used to quantitatively determine an amount of DNA that is present in a test chamber.

One type of biosensor is ion-sensitive field-effect transistor (ISFET). An ion-sensitive field-effect transistor (ISFET) may be used for measuring ion concentrations in solution. For example, when the ion concentration (such as H+) changes, the current through a transistor may change accordingly. Thus, the solution may be used as the gate electrode. When a biospecies (e.g., DNA) lands on the gate dielectric of an ISFET, the charges carried by the biospecies may modulate the electrical current in the channel of the ISFET. Sensing may be achieved by monitoring a change of the transistor characteristics (e.g., threshold voltage (Vt)).

However, relatively small amounts of a biospecies, such as DNA, may carry a relatively small amount of charge. Thus, a Vt shift may be relatively small when the DNA sample is placed in the test chamber.

SUMMARY

According to an exemplary embodiment of the present invention, a vertical biosensor includes a substrate and a source disposed on the substrate. A bottom spacer is disposed on the source. A chamber is disposed on the bottom spacer. A sensing gate dielectric is disposed on side and bottom surfaces of the chamber. A fin channel is disposed on opposite sides of the chamber along a direction parallel to an upper surface of the substrate facing the chamber. A back gate dielectric is disposed on the fin channel. A drain is positioned above the fin channel along a direction orthogonal to an upper surface of the substrate. A thickness of the back gate dielectric is greater than a thickness of the sensing gate dielectric.

According to an exemplary embodiment of the present invention, a biosensor includes a substrate and an insulator disposed on the substrate. A chamber is disposed on the insulator. A sensing gate dielectric is disposed on side and bottom surfaces of the chamber. A source is positioned at first side of the chamber and a drain is positioned at a second side of the chamber. A fin is disposed on opposite sides of the chamber along a direction parallel to an upper surface of the substrate facing the chamber. A back gate dielectric is disposed on the fin. A thickness of the back gate dielectric is greater than a thickness of the sensing gate dielectric.

According to an exemplary embodiment of the present invention, a method of manufacturing a vertical biosensor includes providing a substrate and epitaxially growing a first doped layer, an undoped layer on the first doped layer and a second doped layer on the undoped layer. The method includes forming a mandrel on the second doped layer. The method includes forming a sidewall image transfer spacer on opposite side surfaces of the second doped layer. The method includes etching the first doped layer, the undoped layer and the second doped layer using the mandrel and the sidewall image transfer spacer as a mask. The first doped layer is etched to form a source, the undoped layer is etched to form a channel and the second doped layer is etched to form a drain. The method includes forming a bottom spacer on the source on opposite sides of the channel along a direction parallel to an upper surface of the substrate. The method includes forming a back gate dielectric on the bottom spacer and on opposite sides of the channel along the direction parallel to the upper surface of the substrate. The method includes forming a back gate electrode on the back gate dielectric on opposite sides of the channel along the direction parallel to the upper surface of the substrate. The method includes forming top spacers on the back gate dielectric and the back gate electrode. The method includes epitaxially growing the drain such that the drain becomes wider than the channel along the direction parallel to the upper surface of the substrate. The method includes forming an interval dielectric on the top spacers, the drain and the sidewall image transfer spacers. The method includes removing the mandrel and removing the drain and the channel between the sidewall image transfer spacers to form a chamber space on the source. The method includes forming a second bottom spacer on the source. The method includes forming a sensing gate dielectric on side and bottom surfaces of the chamber space to form a chamber. The sensing gate dielectric has a narrower thickness than a thickness of the back gate dielectric.

BRIEF DESCRIPTION OF THE DRAWINGS

The above and other features of the present invention will become more apparent by describing in detail exemplary embodiments thereof, with reference to the accompanying drawings, in which.

DETAILED DESCRIPTION

Figure 1A:
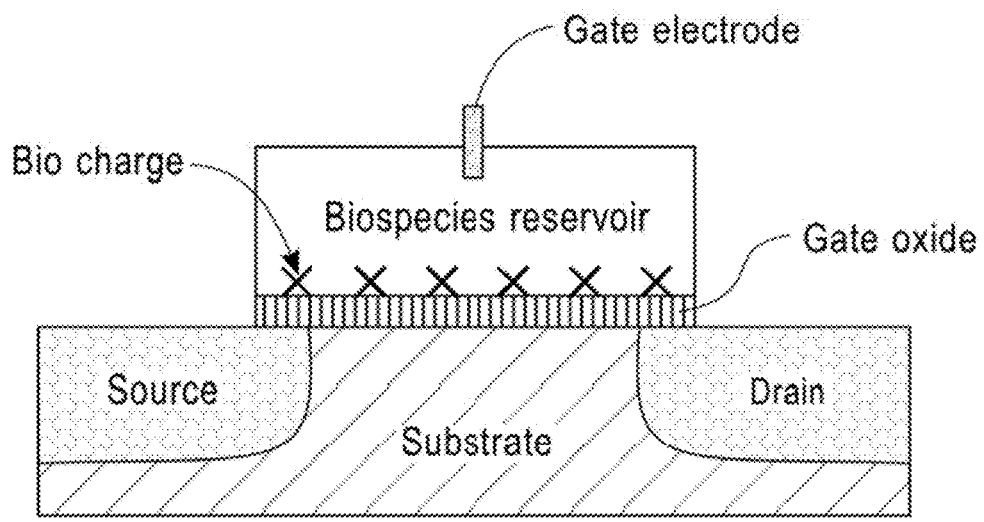
FIG. 1A illustrates a metal-oxide-semiconductor field-effect transistor (MOSFET) employing a conventional threshold voltage (Vt) shift.

It will be understood that the terms "first," "second," "third," etc. are used herein to distinguish one element from another, and the elements are not limited by these terms. Thus, a "first" element in an exemplary embodiment may be described as a "second" element in another exemplary embodiment.

Exemplary embodiments of the present invention will be described more fully hereinafter with reference to the accompanying drawings. Like reference numerals may refer to like elements throughout the specification and drawings.

Exemplary embodiments of the present invention provide a method and a structure to improve the sensitivity of an ion-sensitive field-effect transistor (ISFET) sensor and more specifically, for forming a biosensor using the ISFET sensor with signal amplification. The biosensor according to an exemplary embodiment of the present invention has a vertical fin body and two independent gates on two sides of fin body. The first gate has a thin gate dielectric, functioning as the sensing gate of the biosensor, and the second gate has a thick gate dielectric, functioning as the back gate of the ISFET, as described in more detail below.

The biosensor according to an exemplary embodiment of the present invention may be operated as follows. The sensing gate (reference electrode) is biased at a constant potential. When a biocharge lands on the sensing gate, it causes a Vt shift. The back gate is adjusted to restore the channel current to the same value as the channel current before biospecies landing on the sensing gate. The change of the back gate voltage is measured. Because the back gate dielectric thickness is greater than the sensing gate dielectric, a larger change of back gate voltage is applied to restore the channel current to the reference current. For example, for a double gated FinFET with sensing gate dielectric of ~1 nm and back gate dielectric thickness of ~10 nm, the Vt shift by back gate is ~150 mV/V. Thus, for the same Vt shift, ~7× of back gate voltage is applied. Thus, biosensor sensitivity is increased by ~7×.

Figure 1B:
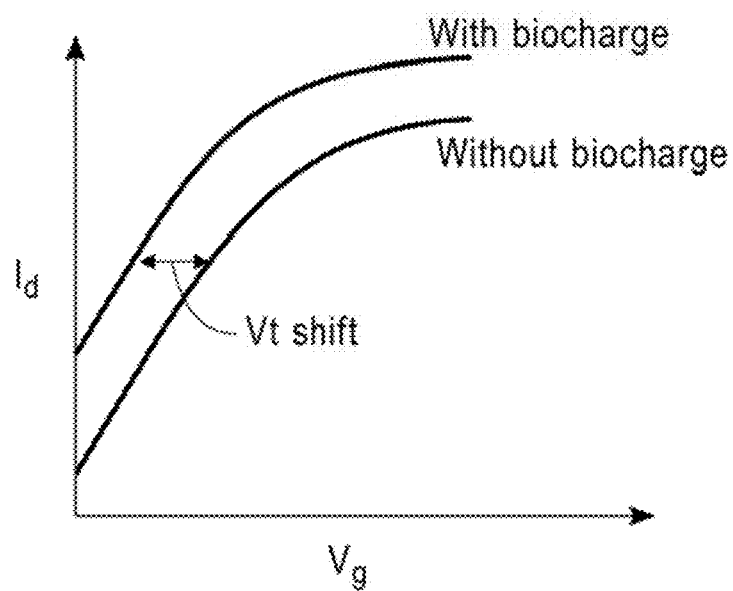
FIG. 1B illustrate a Vt shift in the MOSFET of FIG. 1A.

FIG. 1A illustrates a metal-oxide-semiconductor field-effect transistor (MOSFET) employing a conventional threshold voltage (Vt) shift. FIG. 1B illustrate a Vt shift in the MOSFET of FIG. 1A.

Referring to FIGS. 1 and 1B, one type of biosensors is ion-sensitive field-effect transistor (ISFET) which may be similar to a conventional MOSFET illustrated in FIG. 1A. When a biospecies (e.g., DNA) lands on the gate dielectric of an ISFET, the charges carried by the biospecies modulates the electrical current in the channel of the ISFET. Sensing is achieved by monitoring the change of the transistor characteristics (e.g., threshold voltage (Vt)).

In certain applications, the biospecies carries a relatively small amount of charges. Thus, the Vt shift of the ISFET may be relatively small, resulting in poor sensitivity. Thus, a biosensor, such as an ISFET sensor, having increased sensitivity may more accurately detect a presence of and quantitatively evaluate a biospecies, such as DNA.

Figure 2:
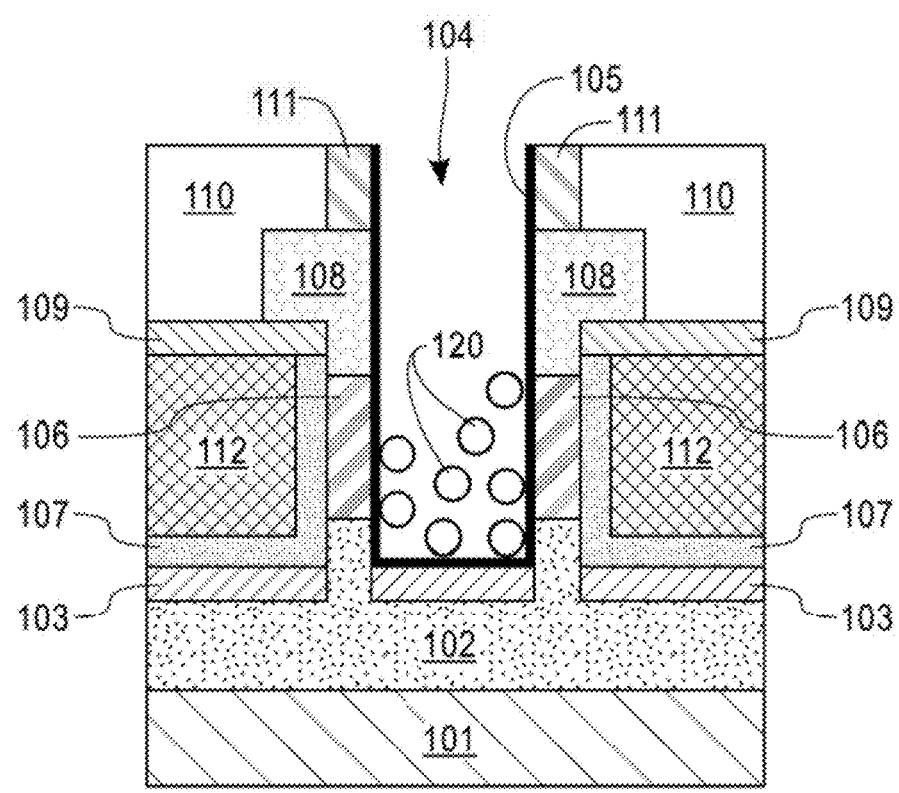
FIG. 2 is a cross-sectional view of a vertical biosensor according to an exemplary embodiment of the present invention.

FIG. 2 is a cross-sectional view of a vertical biosensor according to an exemplary embodiment of the present invention.

Referring to FIG. 2, a back gate dielectric is thicker than the sensing gate dielectric. Thus, when a biospecies lands on the sensing gate, the biocharges cause a Vt shift. To maintain a constant channel current, a higher back gate voltage change is applied. By measuring the back gate voltage change, a higher sensitivity is obtained.

According to an exemplary embodiment of the present invention, a vertical biosensor includes a substrate 101 and a source 102 disposed on the substrate 101. A bottom spacer 103 is disposed on the source 102. A chamber 104 is disposed on the bottom spacer 103. A sensing gate dielectric 105 is disposed on side and bottom surfaces of the chamber 104. A fin channel 106 is disposed on opposite sides of the chamber 104 along a direction parallel to an upper surface of the substrate 101 facing the chamber 104. A back gate dielectric 107 is disposed on the fin channel 106. A drain 108 is positioned above the fin channel 106 along a direction orthogonal to an upper surface of the substrate 101. A thickness of the back gate dielectric 107 is greater than a thickness of the sensing gate dielectric 105.

The thickness of the back gate dielectric 107 being greater than the thickness of the sensing gate dielectric 105 may increase sensitivity of the biosensor. For example, sensing gate dielectric 105 (reference electrode) is biased at a constant potential. When a biocharge (e.g., from a biospecies 120, such as DNA, or a protein) lands on the sensing gate dielectric 105, it causes a Vt shift. The back gate dielectric 107 is adjusted to restore the channel current to the same value as the channel current before biospecies landing on the sensing gate. The change of the back gate voltage is measured. Because the back gate dielectric thickness is greater than the sensing gate dielectric, a larger change of back gate voltage is applied to restore the channel current to the reference current. For example, with a sensing gate dielectric 105 having a thickness of 1 nm and back gate dielectric 107 having a of thickness of 10 nm, the Vt shift by back gate is 150 mV/V. Thus, for the same Vt shift, 7 times of back gate voltage is applied. This is equivalent to improve the biosensor sensitivity by 7 times. Thus, the thickness of the back gate dielectric 107 is at least ten times as thick as the thickness of the sensing gate dielectric 105 along the direction parallel to the upper surface of the substrate 101 facing the chamber 104. The same thickness variation may similarly be applied along the direction orthogonal to the upper surface of the substrate 101. In some exemplary embodiments of the present invention, the sensing gate dielectric 105 has a thickness ranging from 1 nm to 3 nm, and the back gate dielectric 107 has a thickness at least 3 times of the sensing gate dielectric thickness, for example, 10 times that of the sensing gate dielectric thickness. Thus, the Vt shift may be indirectly measured to increase sensitivity of the biosensor.

According to an exemplary embodiment of the present invention, a back gate electrode 112 may be disposed on the back gate dielectric 107. A top spacer 109 may be disposed on the back gate dielectric 107. An interval dielectric (ILD) 110 may be disposed on the top spacer 109.

According to an exemplary embodiment of the present invention, a sidewall image transfer (SIT) spacer 111 may be positioned above the drain 108. A thickness of the sidewall image transfer spacer 111 may be the same as a thickness of the fin channel 106 along the direction parallel to the upper surface of the substrate 101 facing the chamber 104. The drain 108 and/or the SIT spacer 111 may be in direct contact with the sidewall of the sensing gate dielectric 105 facing away from the chamber 104.

According to an exemplary embodiment of the present invention, the SIT spacers 111 described herein may include silicon nitride. The SIT spacers 111 may be used to form the fins described herein.

According to an exemplary embodiment of the present invention, the biospecies 120 may include DNA, a protein, or a cancer cell.

Figure 3A:
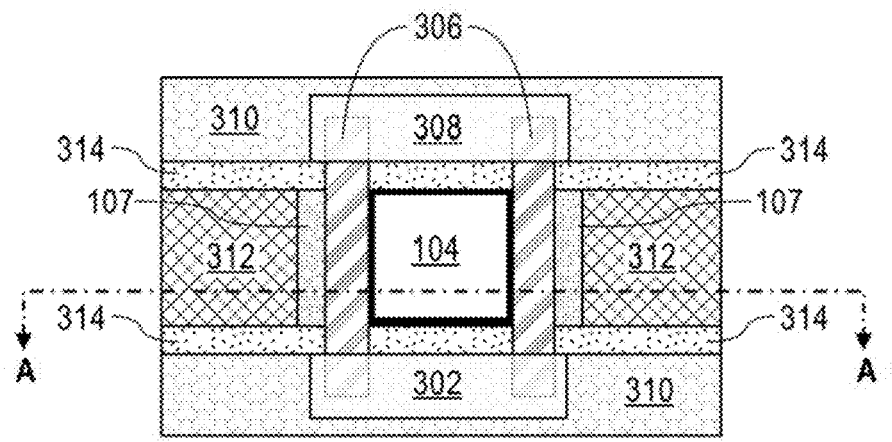
FIG. 3A is a top down view of a Fin Field Effect Transistor (finFET) biosensor according to an exemplary embodiment of the present invention.
Figure 3B:
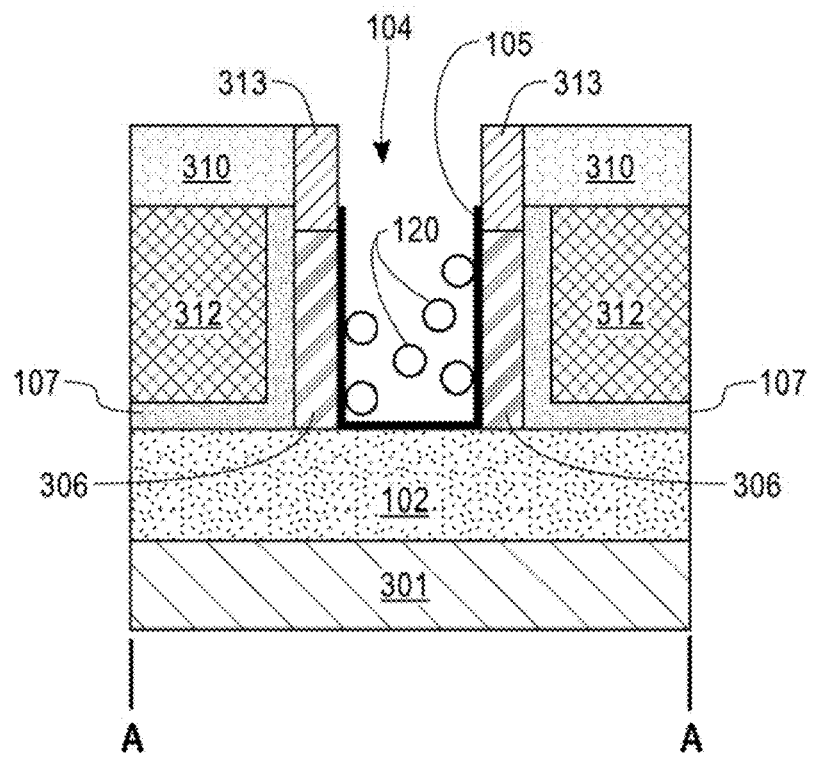
FIG. 3B is a cross-sectional view along line A-A of FIG. 3A.

FIG. 3A is a top down view of a Fin Field Effect Transistor (finFET) biosensor according to an exemplary embodiment of the present invention. FIG. 3B is a cross-sectional view along line A-A of FIG. 3A.

Referring to FIG. 3A and FIG. 3B, according to an exemplary embodiment of the present invention, instead of a vertical transistor, a finFET can be used with two independent gates, where the sensing gate has thin gate dielectric and the back gate has thick gate dielectric, as described in more detail below.

According to an exemplary embodiment of the present invention, a biosensor includes a substrate 101 and an insulator 301 disposed on the substrate 101. A chamber 104 is disposed on the insulator 301. A sensing gate dielectric 105 is disposed on side and bottom surfaces of the chamber 104. A source 302 is positioned at first side of the chamber 104 and a drain 308 is positioned at a second side of the chamber 104. A fin 306 is disposed on opposite sides of the chamber 104 along a direction parallel to an upper surface of the substrate 101 facing the chamber 104. A back gate dielectric 107 is disposed on the fin 306. A thickness of the back gate dielectric 107 is greater than a thickness of the sensing gate dielectric 105.

According to an exemplary embodiment of the present invention, the insulator 301 may be a buried oxide insulator or an STI spacer.

According to an exemplary embodiment of the present invention, the thickness of the back gate dielectric 107 is at least ten times as thick as the thickness of the sensing gate dielectric 105 along the direction parallel to the upper surface of the substrate 101 facing the chamber 104.

According to an exemplary embodiment of the present invention, a back gate electrode 312 may be disposed on the back gate dielectric 107.

According to an exemplary embodiment of the present invention, an interval dielectric 310 may be positioned above the back gate dielectric 107. A fin cap 313 may be disposed on an upper surface of the fin 306. A thickness of the fin cap 313 may be the same as a thickness of the fin 306 along the direction parallel to the upper surface of the substrate 101 facing the chamber 104.

According to an exemplary embodiment of the present invention, a threshold voltage (Vt) shift may occur when a biospecies (e.g., 120) comes into contact with the sensing gate dielectric 105, as described in more detail above. A back gate voltage may be applied to the back gate dielectric 107 to compensate for the Vt shift. The back gate dielectric 107 is configured to detect the back gate voltage, as described in more detail above.

According to an exemplary embodiment of the present invention, the biospecies 120 may include DNA, a protein, or a cancer cell.

According to an exemplary embodiment of the present invention, a spacer 314 may be disposed on the source 302 between the source 302 and the back gate electrode 312. The spacer 314 may include a plurality of spacers separating the source and the drain from the chamber 104, such that the fin 306 is in contact with the sensing gate dielectric 105 lining the outside of the chamber 104.

A manufacturing method in which the biosensor according to an exemplary embodiment of the present invention will be described in more detail below for reference to FIGS. 4A, 4B and 5-13. According to the method described below, the biosensor can be formed along with vertical transistor CMOS. Thus, a lab-on-chip with both the biosensor and a CMOS logic/memory can be integrated on the same chip.

Figure 4A:
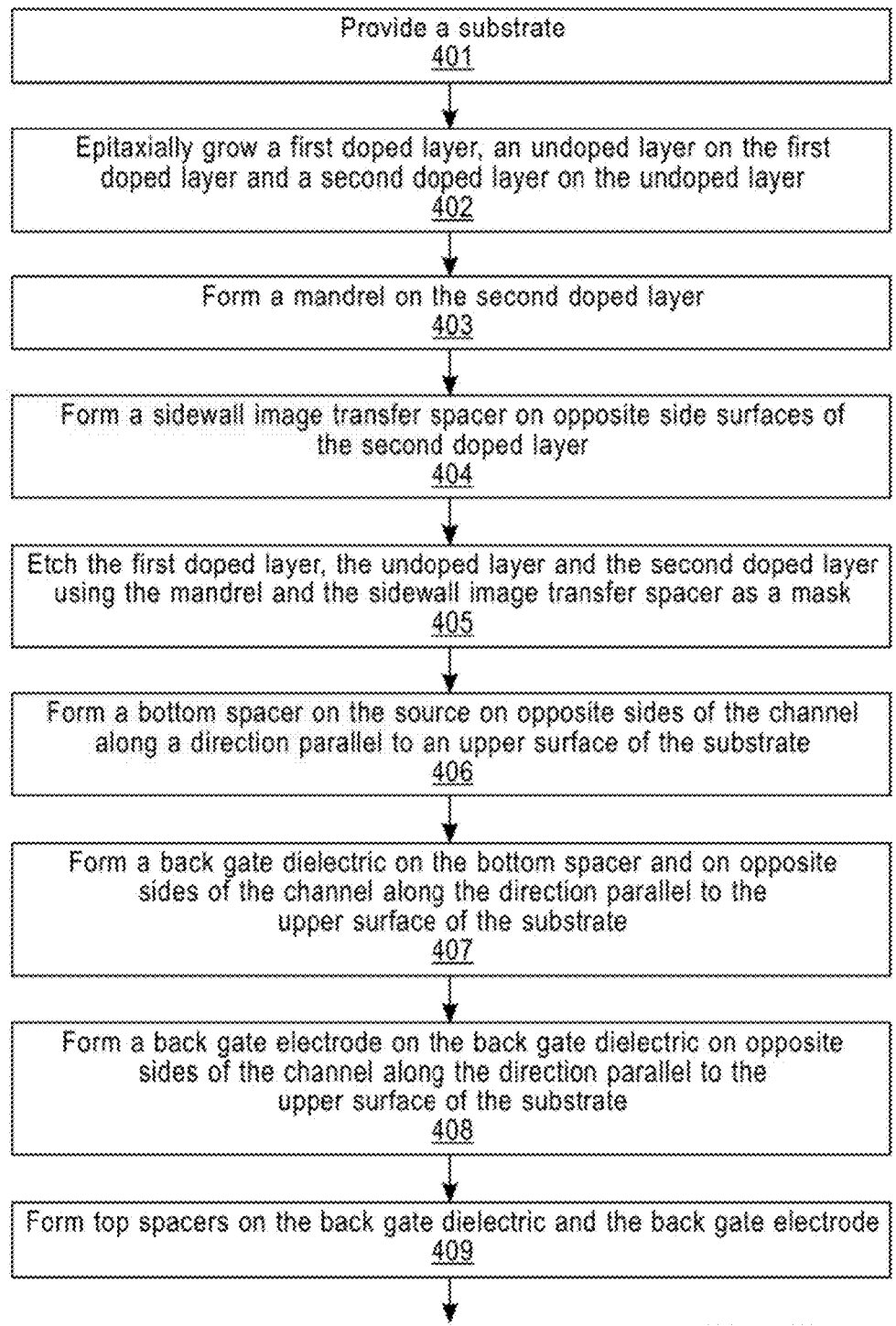
FIGS. 4A and 4B illustrate a flowchart of a method of forming the vertical biosensor of FIG. 2 according to an exemplary embodiment of the present invention.
Figure 4B:
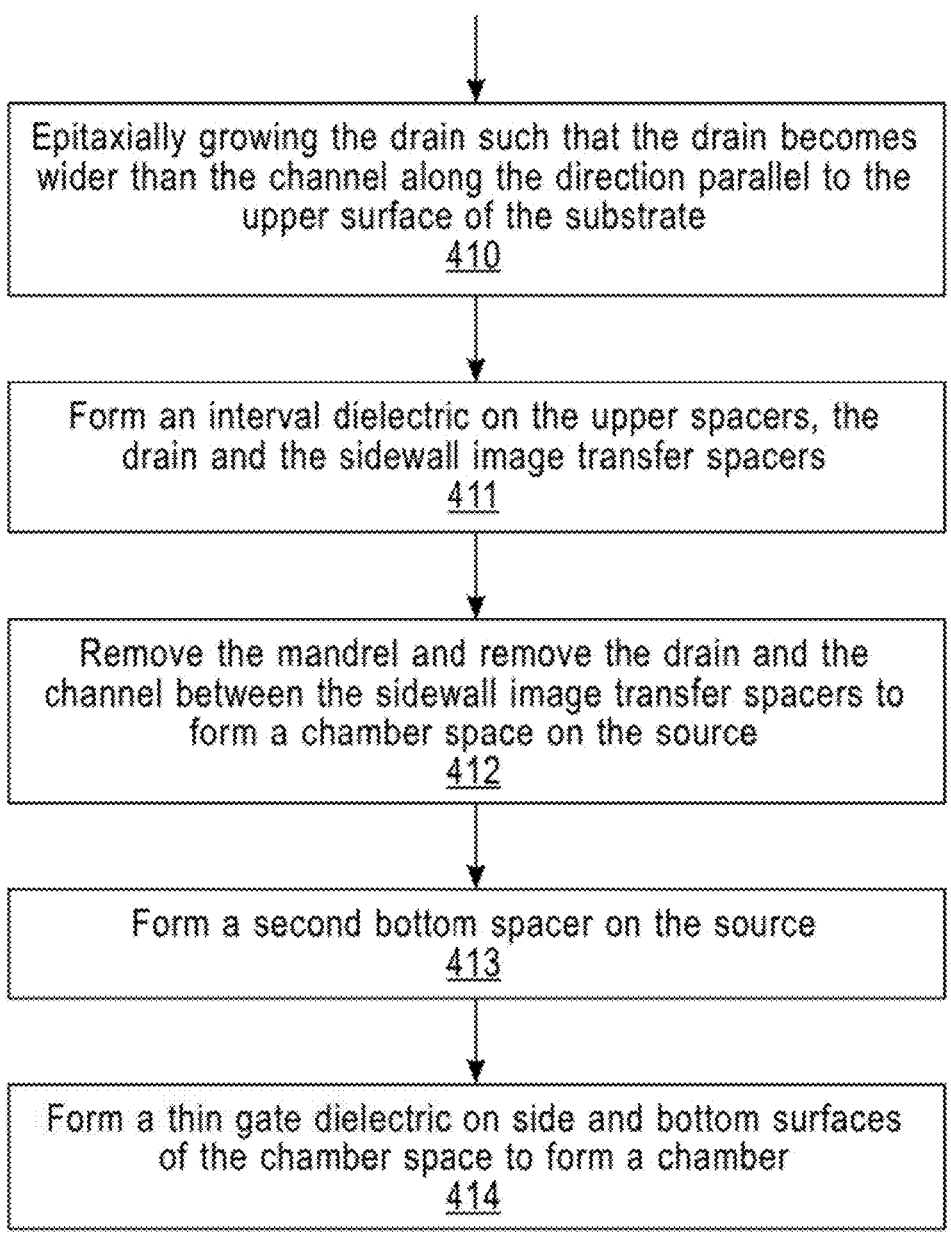
Figure 5:
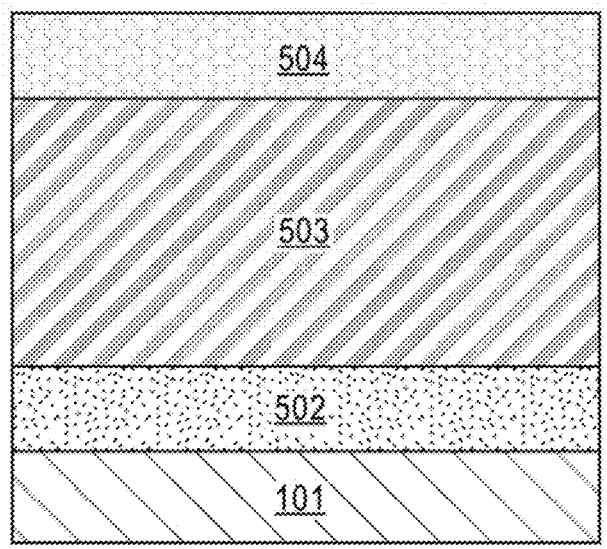
FIGS. 5-13 are cross-sectional views illustrating the method of forming the vertical biosensor of FIG. 2 according to an exemplary embodiment of the present invention.
Figure 6:
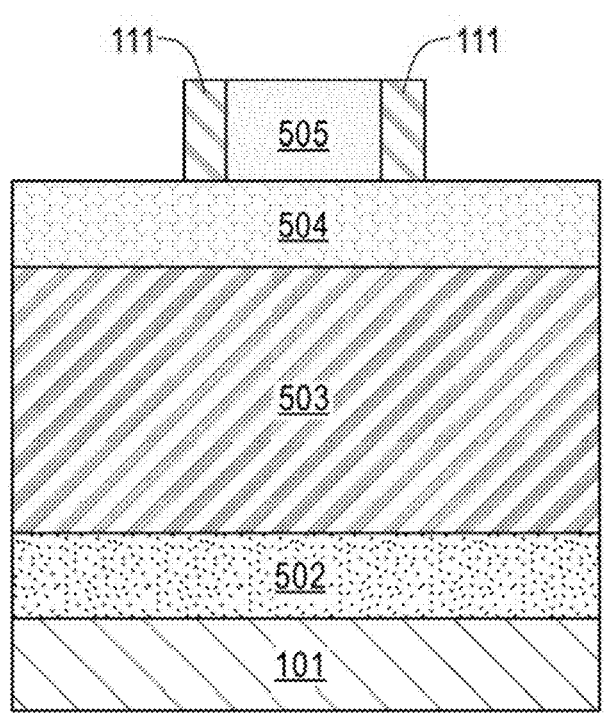
Figure 7:
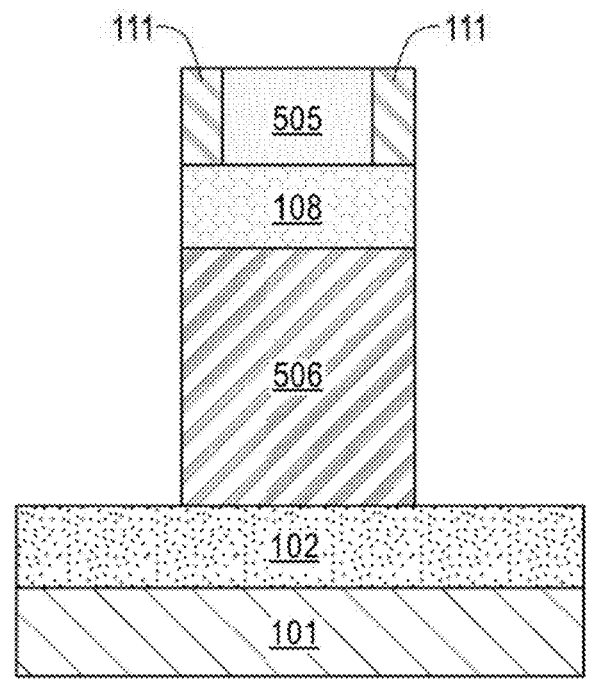
Figure 8:
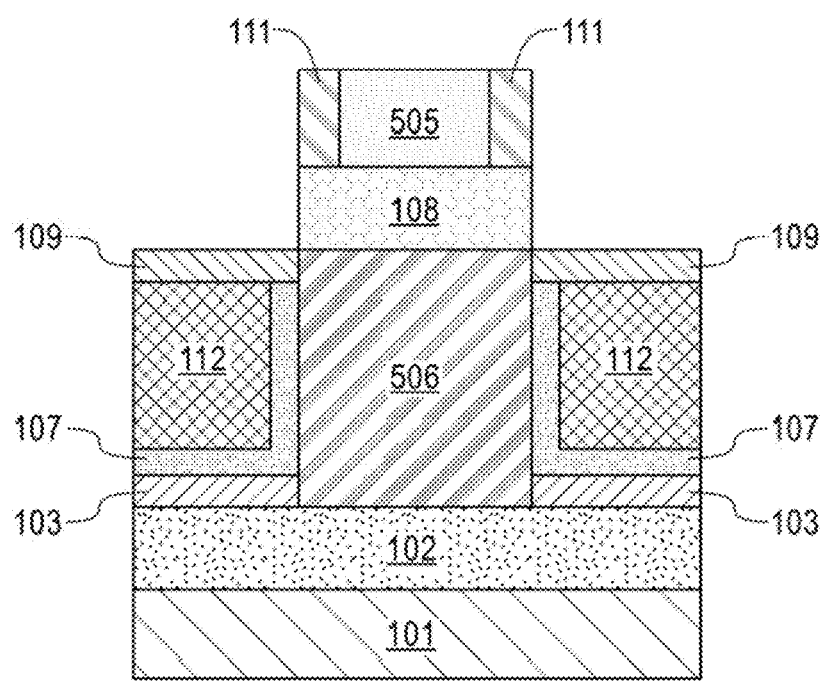
Figure 9:
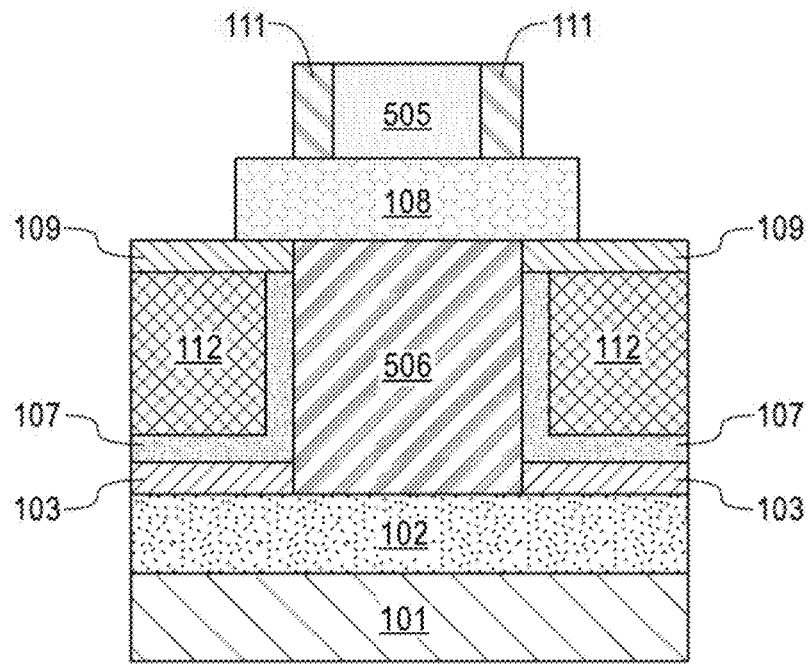
Figure 10:
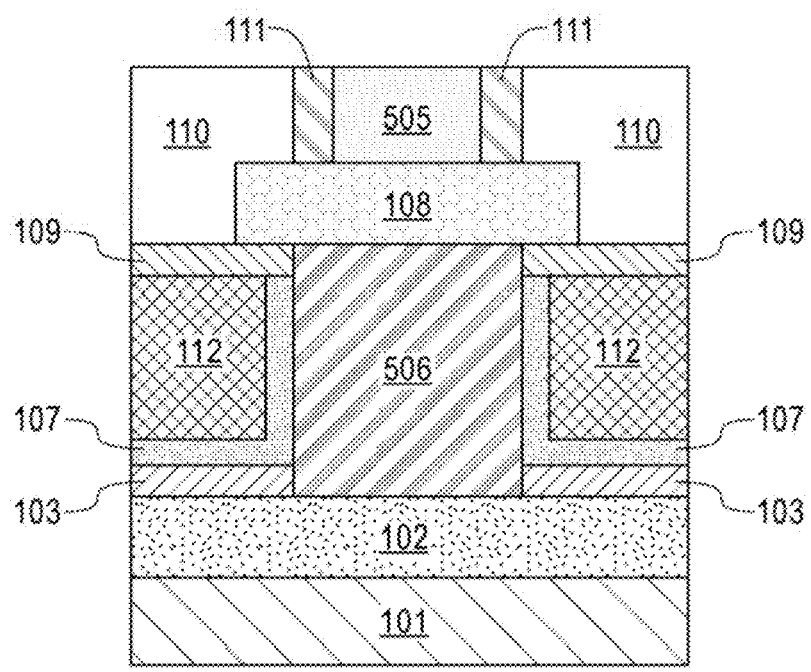
Figure 11:
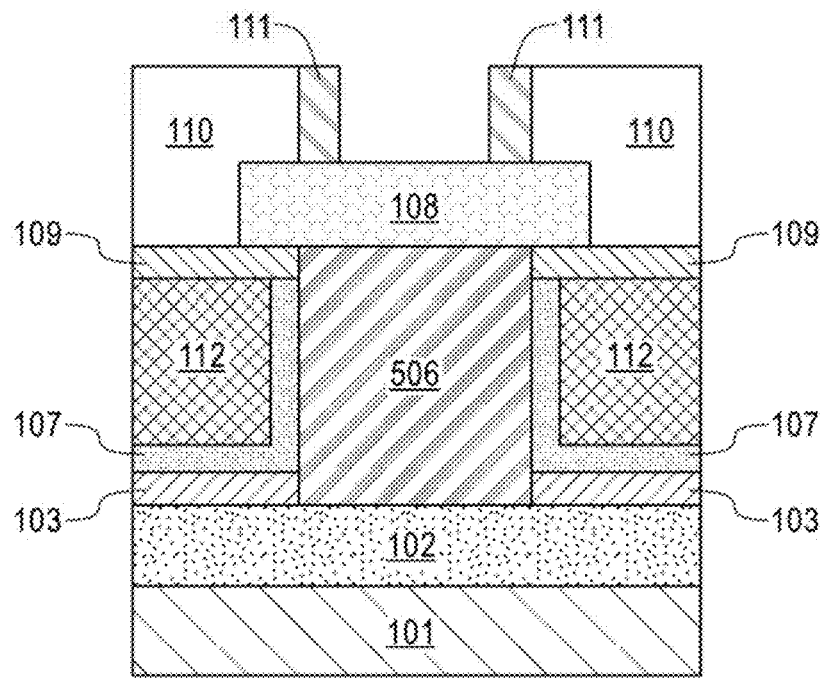
Figure 12:
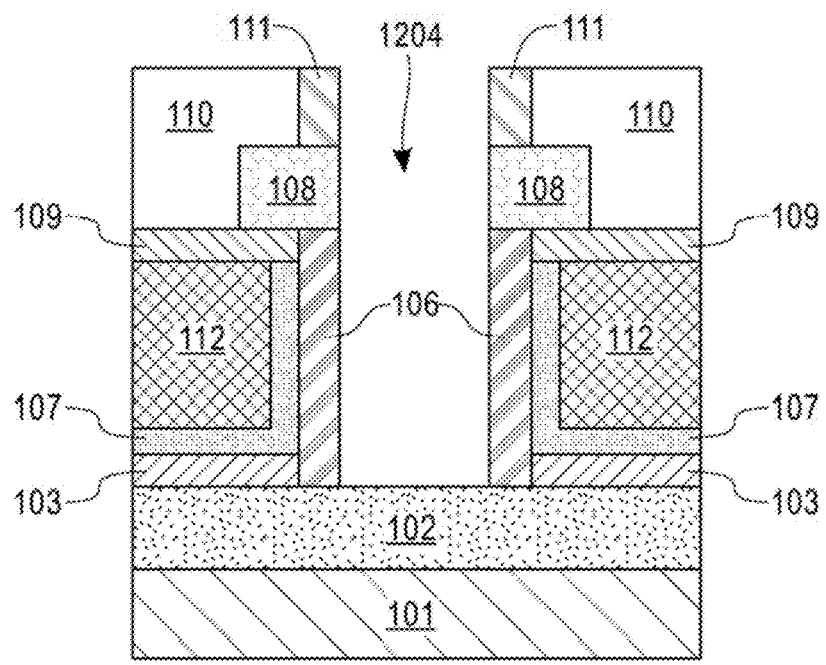
Figure 13:
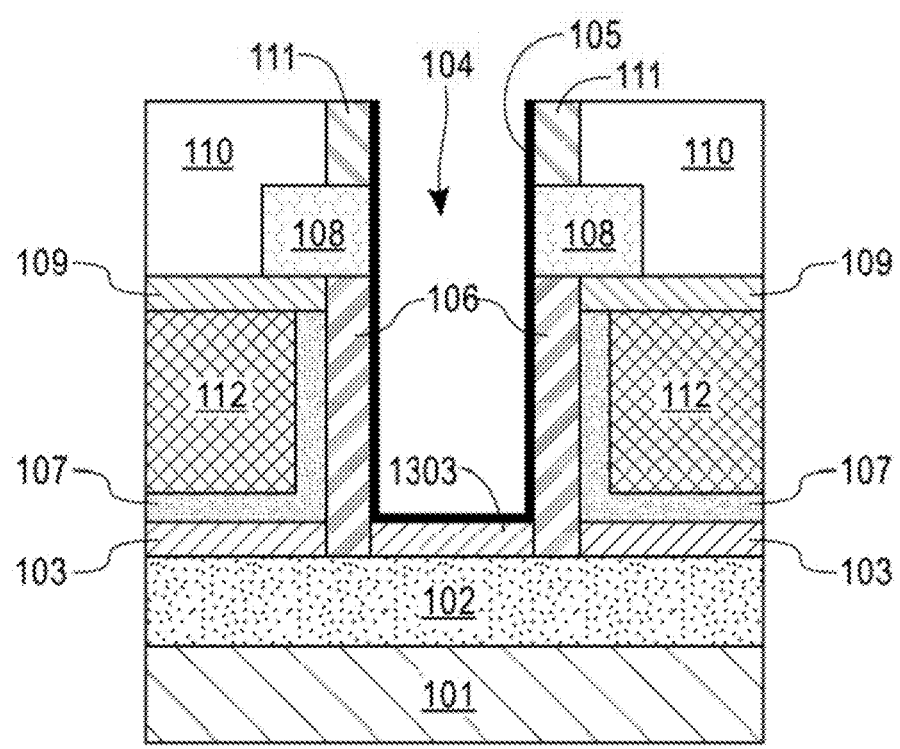

FIGS. 4A and 4B illustrate a flowchart of a method of forming the vertical biosensor of FIG. 2 according to an exemplary embodiment of the present invention. FIGS. 5-13 are cross-sectional views illustrating the method of forming the vertical biosensor of FIG. 2 according to an exemplary embodiment of the present invention.

Referring to FIGS. 4A, 4B and 5-13, according to an exemplary embodiment of the present invention, a method of manufacturing a vertical biosensor includes providing a substrate 101 (step 401) and epitaxially growing a first doped layer 502, an undoped layer 503 on the first doped layer and a second doped layer 504 on the undoped layer (step 402). The method includes forming a mandrel 505 on the second doped layer (step 403). The method includes forming a sidewall image transfer (SIT) spacer 111 on opposite side surfaces of the second doped layer (step 404). The method includes etching the first doped layer, the undoped layer and the second doped layer using the mandrel and the sidewall image transfer spacer 111 as a mask (step 405). The first doped layer 502 is etched to form a source 102, the undoped layer 503 is etched to form a channel 506 and the second doped layer 504 is etched to form a drain 108. The method includes forming a bottom spacer 103 on the source on opposite sides of the channel 506 along a direction parallel to an upper surface of the substrate 101 (step 406). The method includes forming a back gate dielectric 107 on the bottom spacer 103 and on opposite sides of the channel 506 along the direction parallel to the upper surface of the substrate 101 (step 407). The method includes forming a back gate electrode 112 on the back gate dielectric 107 on opposite sides of the channel 506 along the direction parallel to the upper surface of the substrate 101 (step 408). The method includes forming top spacers 109 on the back gate dielectric 107 and the back gate electrode 112 (step 409). The method includes epitaxially growing the drain 108 such that the drain 108 becomes wider than the channel 506 along the direction parallel to the upper surface of the substrate 101 (step 410). The method includes forming an interval dielectric 110 on the top spacers 109, the drain 108 and the sidewall image transfer spacers 111 (step 411). The method includes removing the mandrel 505 and removing the drain 108 and the channel 506 between the sidewall image transfer spacers 111 to form a chamber space 1204 on the source 102 (step 412). The method includes forming a second bottom spacer 1303 on the source 102 (step 413). The method includes forming a sensing gate dielectric 105 on side and bottom surfaces of the chamber space 1204 to form a chamber 104 (step 414).

Exemplary Dimensions of the Biosensor According to an Exemplary Embodiment of the Present Invention Fin width: 4 nm to 20 nm, for example, 5 nm to 10 nm. Chamber width: 10 nm to 2000 nm, for example, 50 nm to 200 nm. Sensing gate dielectric thickness: 1 nm to 5 nm, for example, 1 nm to 3 nm. Back gate dielectric thickness: at least 3 times of the thickness of the sensing gate dielectric, for example, at least 10 times the thickness of the sensing gate dielectric. Doped layer thickness (layers 502 and 504): 10 nm to 100 nm, for example, 20 to 40 nm. Undoped layer (layer 503) thickness: 15 nm to 200 nm, for example, 30 nm to 100 nm. However, exemplary embodiments of the present invention are not limited thereto, and other dimensions may be employed.

Material choice: layers 502, 503, 504: semiconductors including but not limited to silicon, germanium, silicon germanium, silicon carbide, III-V compound semiconductors, or II-VI compound semiconductors. Dopants in 502 and 504 can be n-type dopants or p-type dopants. For silicon, silicon germanium, germanium, n-type dopants include phosphorus, arsenic, indium and p-type dopants include boron, gallium. Layers 502, 503, 504 can be formed by epitaxy growth. However, exemplary embodiments of the present invention are not limited thereto, and other materials may be employed Substrate 101: Silicon, germanium, silicon germanium, silicon carbide, and III-V compound semiconductors, or II-VI compound semiconductors. The semiconductor substrate 101 may also include an organic semiconductor or a layered semiconductor such as, for example, Si/SiGe, a silicon-on-insulator or a SiGe-on-insulator. A portion or entire semiconductor substrate 101 may be amorphous, polycrystalline, or monocrystalline. In addition to the aforementioned types of semiconductor substrates, the semiconductor substrate 101 may also include a hybrid oriented (HOT) semiconductor substrate in which the HOT substrate has surface regions of different crystallographic orientation. The semiconductor substrate 101 may be doped, undoped or contain doped regions and undoped regions therein. The semiconductor substrate 101 may include regions with strain and regions without strain therein, or may include regions of tensile strain and compressive strain. However, exemplary embodiments of the present invention are not limited thereto, and other materials and configurations may be employed Sensing gate dielectric/back gate dielectric (105 and 107): silicon oxide, silicon nitride, silicon oxynitride, boron nitride, high-k materials, or any combination of these materials. Examples of high-k materials include but are not limited to metal oxides such as hafnium oxide, hafnium silicon oxide, hafnium silicon oxynitride, lanthanum oxide, lanthanum aluminum oxide, zirconium oxide, zirconium silicon oxide, zirconium silicon oxynitride, tantalum oxide, titanium oxide, barium strontium titanium oxide, barium titanium oxide, strontium titanium oxide, yttrium oxide, aluminum oxide, lead scandium tantalum oxide, or lead zinc niobate. The high-k may further include dopants such as lanthanum, or aluminum. However, exemplary embodiments of the present invention are not limited thereto, and other materials may be employed Back gate electrode 112: doped polycrystalline or amorphous silicon, germanium, silicon germanium, a metal (e.g., tungsten, titanium, tantalum, ruthenium, zirconium, cobalt, copper, aluminum, lead, platinum, tin, silver, gold), a conducting metallic compound material (e.g., tantalum nitride, titanium nitride, tantalum carbide, titanium carbide, titanium aluminum carbide, tungsten silicide, tungsten nitride, ruthenium oxide, cobalt silicide, nickel silicide), carbon nanotube, conductive carbon, graphene, or any suitable combination of these materials. The conductive material may further include dopants that are incorporated during or after deposition. The back gate electrode may further include a work function setting layer, including but not limited to titanium nitride (TiN), hafnium nitride (HfN), hafnium silicon nitride (HfSiN), tantalum nitride (TaN), tantalum silicon nitride (TaSiN), tungsten nitride (WN), molybdenum nitride (MoN), niobium nitride (NbN); a carbide, including but not limited to titanium carbide (TiC) titanium aluminum carbide (TiAlC), tantalum carbide (TaC), hafnium carbide (HfC), or combinations thereof. However, exemplary embodiments of the present invention are not limited thereto, and other materials may be employed According to an exemplary embodiment of the present invention, the thickness of the back gate dielectric 107 is at least ten times the thickness of the sensing gate dielectric 105 along the direction parallel to the upper surface of the substrate 101 facing the chamber 104. For example, the back gate dielectric 107 may have a thickness of about 10 nm.

According to an exemplary embodiment of the present invention, the sidewall image transfer spacers 111 formed on the second doped layer 504 may include silicon nitride.

According to an exemplary embodiment of the present invention, the mandrel 505 may be an amorphous silicon mandrel including a silicon nitride cap.

According to an exemplary embodiment of the present invention, a back gate voltage may be applied to the back gate dielectric 107 to compensate for a threshold voltage (Vt) shift. The back gate dielectric 107 may be configured to detect the back gate voltage. The back gate dielectric 107 is adjusted to restore the channel current to the same value as the channel current before biospecies landing on the sensing gate. The change of the back gate voltage is measured. Because the back gate dielectric thickness is greater than the sensing gate dielectric, a larger change of back gate voltage is applied to restore the channel current to the reference current. For example, with a sensing gate dielectric 105 having a thickness of 1 nm and back gate dielectric 107 having a of thickness of 10 nm, the Vt shift by back gate is 150 mV/V. Thus, for the same Vt shift, 7 times of back gate voltage is applied. This is equivalent to improve the biosensor sensitivity by 7 times. Thus, the thickness of the back gate dielectric 107 is at least ten times as thick as the thickness of the sensing gate dielectric 105 along the direction parallel to the upper surface of the substrate 101 facing the chamber 104. The same thickness variation may similarly be applied along the direction orthogonal to the upper surface of the substrate 101. Thus, the Vt shift may be indirectly measured to increase sensitivity of the biosensor.

While the present invention has been particularly shown and described with reference to exemplary embodiments thereof, it will be understood by those of ordinary skill in the art that various changes in form and detail may be made therein without departing from the spirit and scope of the present invention as defined by the following claims.

The invention claimed is:

1. A vertical biosensor, comprising:
   a substrate;
   a source disposed on the substrate;
   a bottom spacer disposed on the source;
   a chamber disposed on the bottom spacer, wherein a sensing gate dielectric is disposed on side and bottom surfaces of the chamber;
   a fin channel disposed on opposite sides of the chamber along a direction parallel to an upper surface of the substrate facing the chamber;
   a back gate dielectric disposed on the fin channel; and
   a drain positioned above the fin channel along a direction orthogonal to an upper surface of the substrate,
   wherein a thickness of the back gate dielectric is greater than a thickness of the sensing gate dielectric.

2. The vertical biosensor of claim 1, wherein the thickness of the back gate dielectric is at least ten times as thick as the thickness of the sensing gate dielectric along the direction parallel to the upper surface of the substrate facing the chamber.

3. The vertical biosensor of claim 2, further comprising a top spacer disposed on the back gate dielectric, and an interval dielectric disposed on the top spacer.

4. The vertical biosensor of claim 3, further comprising a sidewall image transfer spacer positioned above the drain, wherein a thickness of the sidewall image transfer spacer is the same as a thickness of the fin channel along the direction parallel to the upper surface of the substrate facing the chamber.

5. The vertical biosensor of claim 2, wherein a threshold voltage (Vt) shift occurs when a biospecies comes into contact with the sensing gate dielectric.

6. The vertical biosensor of claim 5, wherein a back gate voltage is applied to the back gate dielectric to compensate for the Vt shift, and wherein the back gate dielectric is configured to detect the back gate voltage.

7. The vertical biosensor of claim 6, wherein the biospecies includes DNA, a protein, or a cancer cell.

8. A biosensor, comprising:

a substrate;

an insulator disposed on the substrate;

a chamber disposed on the insulator, wherein a sensing gate dielectric is disposed on side and bottom surfaces of the chamber;

a source positioned at first side of the chamber and a drain positioned at a second side of the chamber;

a fin disposed on opposite sides of the chamber along a direction parallel to an upper surface of the substrate facing the chamber;

a back gate dielectric disposed on the fin, wherein a thickness of the back gate dielectric is greater than a thickness of the sensing gate dielectric; and an interval dielectric positioned above the back gate dielectric, and a fin cap disposed on an upper surface of the fin, wherein a thickness of the fin cap is the same as a thickness of the fin along the direction parallel to the upper surface of the substrate facing the chamber.

9. The biosensor of claim 8, wherein the thickness of the back gate dielectric is at least ten times as thick as the thickness of the sensing gate dielectric along the direction parallel to the upper surface of the substrate facing the chamber.

10. The biosensor of claim 9, further comprising a back gate electrode disposed on the back gate dielectric.

11. The biosensor of claim 9, wherein a threshold voltage (Vt) shift occurs when a biospecies comes into contact with the sensing gate dielectric.

12. The biosensor of claim 11, wherein a back gate voltage is applied to the back gate dielectric to compensate for the Vt shift, and wherein the back gate dielectric is configured to detect the back gate voltage.

13. The biosensor of claim 12, wherein the biospecies includes DNA, a protein, or a cancer cell.

\* \* \* \* \*